_United States Patent_ [19]

Petruck et al.

[11] 4,456,777

[45] Jun. 26, 1984

[54] PROCESS FOR THE PREPARATION OF 2-CHLORO-4-NITROTOLUENE

[75] Inventors: Gerd-Michael Petruck, Erkrath, Fed. Rep. of Germany; Paul R. Wambach, deceased, late of Leverkusen, Fed. Rep. of Germany, by Christa Wambach, heiress; Adolf Wissner, Leverkusen, Fed. Rep. of Germany

[73] Assignee: Bayer Aktiengesellschaft, Leverkusen, Fed. Rep. of Germany

[21] Appl. No.: 392,450

[22] Filed: Jun. 28, 1982

[30] Foreign Application Priority Data

Jul. 18, 1981 [DE] Fed. Rep. of Germany ....... 3128442

[51] Int. Cl.³ ............................................. C07C 79/12
[52] U.S. Cl. .................................................. 568/937
[58] Field of Search ............................... 568/937, 938

[56] References Cited

U.S. PATENT DOCUMENTS 3,005,031 10/1961 Friedrich ........................... 568/938
3,256,350 6/1966 McCall et al. ..................... 568/938
3,423,475 1/1969 Weinstock et al. ................ 568/938
3,917,723 11/1975 Szczepanski et al. ............. 568/937
4,327,036 4/1982 Marsh ............................. 260/465 G

FOREIGN PATENT DOCUMENTS 2156285 3/1973 Fed. Rep. of Germany ...... 568/937
50-7589 3/1975 Japan ................................. 568/937

OTHER PUBLICATIONS

Chemical Abstracts, vol. 83, No. 13, Sep. 29, 1975, p. 511, Nr. 113927q.

_Primary Examiner_—Leland A. Sebastian
_Attorney, Agent, or Firm_—Sprung, Horn, Kramer & Woods

[57] ABSTRACT

A process for the preparation of 2-chlor-4-nitrotoluene is disclosed by chlorination of 4-nitrotoluene in the presence of iodine. The resultant 2-chloro-4-nitrotoluene is a valuable intermediate for the preparation of herbicides.

9 Claims, No Drawings

PROCESS FOR THE PREPARATION OF 2-CHLORO-4-NITROTOLUENE

The invention relates to a process for the preparation of 2-chloro-4-nitrotoluene by chlorination of 4-nitrotoluene.

Chlorination of 4-nitrotoluene in the presence of anhydrous iron(III) chloride (J. Chem. Soc. 1927, 2903) and antimony(V) chloride (Bull. Soc. chim. belges 61, 317 (1952)), and also in the presence of iodine in combination with iron (ratio 1:10) (Naturwiss. 17, 13 (1929) and Houben-Weyl, Methoden der organischen Chemie (Methods of organic chemistry), Volume V/3, 704 (1962)) and in the presence of iron(III) chloride and iodine (Japanese Published Specification 75/7589) or in the presence of iron, iodine and phosphorus trichloride (U.S. Pat. No. 3,005,031) is known.

The disadvantage of these processes is that undesired by-products are formed in considerable amounts and the desired 2-chloro-4-nitrotoluene is produced only in unsatisfactory amounts. In addition, the separation and isolation of the 2-chloro-4-nitrotoluene from the by-products requires expensive separation procedures, which has a severe adverse effect on the economics of the processes mentioned. For example, the desired 2-chloro-4-nitrotoluene is obtained by the chlorination of 4-nitrotoluene in the presence of iron and iodine (weight ratio 10:1) with a maximum of only 95.1%, whilst undesired by-products are formed in substantial amounts, that is, at least 2.6% (see comparison example).

A process for the preparation of 2-chloro-4-nitrotoluene by chlorination of 4-nitrotoluene has now been found which is characterised in that the chlorination is carried out at temperatures from the melting point of the product employed up to 120° C. with 0.6 to 1.2 mol of chlorine per mol of product employed in the presence of 0.1 to 10% by weight of iodine relative to product employed.

It is possible to employ both pure 4-nitrotoluene and technical 4-nitrotoluene in the process according to the invention.

In the process according to the invention, 0.7 to 1.05 mol of chlorine is preferably employed per mol of 4-nitrotoluene employed, and particularly preferably 0.9 to 1.0 mol of chlorine.

The reaction according to the invention is preferably carried out in the presence of 0.3 to 1% by weight of iodine relative to the 4-nitrotoluene employed. Preferably technical grade iodine is employed which shows the advantage of the lower price.

The process according to the invention is preferably carried out at 50° to 100° C., particularly preferably at 60° to 80° C.

The process according to the invention can be carried out with or without solvents. Solvents which can be employed are those customary for nuclear chlorination, for example chlorinated hydrocarbons, such as methylene chloride, carbon tetrachloride, ethylene chloride, tetrachloroethane, trichlorobenzenes and/or tetrachlorobenzenes. The chlorination is preferably carried out in the absense of a solvent.

The process according to the invention can be carried out at atmospheric pressure or elevated pressure, e.g. at 1 to 10 bar. Atmospheric pressure is preferably employed.

The process according to the invention can be carried out continuously or discontinuously.

The process according to the invention can be carried out in a manner such that chlorine is added to 4-nitrotoluene and iodine initially introduced, or a solution of iodine and chlorine is simultaneously metered in to the 4-nitrotoluene initially introduced. For this purpose, iodine and chlorine can be dissolved in the abovementioned organic solvents.

A preferred embodiment of the process according to the invention is as follows:

0.6 to 1.2 mol of chlorine per mole of 4-nitrotoluene is passed into a mixture of 4-nitrotoluene and iodine. Preferably gaseous chlorine is introduced into the reaction mixture. The iodine is then washed out of the reaction mixture with water or, particularly advantageously, with a solution of potassium iodide or sodium bisulphite. A product is obtained which has a particularly high proportion of 2-chloro-4-nitrotoluene (more than 98%) and only a small proportion of by-products (less than 1.4%).

This is all the more surprising since it is known from J. Chem. Soc. 121, 806 (1922) that in the chlorination of 2-chloro-4-nitrotoluene to give 2,6-dichloro-4-nitrotoluene in the presence of iodine a particularly high proportion of by-products chlorinated in the side-chain is formed.

2-Chloro-4-nitrotoluene is an intermediate for the herbicide Chlortoluron (Pesticide Manual of the Brit. Crop Protection Council; Belgian Pat. No. 728,267).

The following examples are intended to illustrate the process according to the invention, without however restricting it to these.

EXAMPLE 1

6850 g (49.9 mol) of 4-nitrotoluene are chlorinated in the presence of 34.2 g (0.5% by weight) of iodine at 60° C. up to a density $D_4^{60}$ of 1.29 g/cm$^3$. About 1 mol of chlorine is reacted per mol of 4-nitrotoluene. Analysis by gas chromatography gives:
98.1% of 2 chloro-4-nitrotoluene
1.4% of 4-nitrotoluene
0.5% of by-products
Yield: 8423 g (49.1 mol; 98.3% relative to the 4-nitrotoluene employed).

EXAMPLE 2

685 g (5 mol) of 4-nitrotoluene are chlorinated in the presence of 6.9 g (1% by weight) of iodine in a glass flask at 80° C. up to a density of about 1.280 (at the reaction temperature). About 1 mol of chlorine per mol of 4-nitrotoluene was reacted in this process.
Analysis by gas chromatography gives:
98.2% of 2-chloro-4-nitrotoluene
0.4% of 4-nitrotoluene
1.4% of by-products
Yield: 848 g (4.94 mol; 98.8% relative to the 4-nitrotoluene employed)

EXAMPLE 3

731 g (5.33 mol) of 4-nitrotoluene are chlorinated in the presence of 7.3 g (1% by weight) of iodine in a bubble column of glass (level (gassed) 110 cm; diameter 3 cm) at 70° to 80° C. At a density of $D_4^{70}$ of about 1.295 g/cm$^3$, analysis by gas chromatography gave:
97.4% of 2-chloro-4-nitrotoluene
1.4% of 4-nitrotoluene
1.2% of by-products Yield: 906 g (5.28 mol; 99.1% relative to the 4-nitrotoluene employed).

EXAMPLE 4

(comparison example with FeCl$_3$/I$_2$)

1370 g (10 mol) of 4-nitrotoluene are chlorinated in the presence of 13.7 g (1.0% by weight) of iron(III) chloride and 1.4 g (0.1% by weight) of iodine at 70° C. At a density $D_4^{70}$ of 1.287 g/cm$^3$, analysis by gas chromatography gave:

95.1% of 2-chloro-4-nitrotoluene
2.3% of 4-nitrotoluene
2.6 % of by-products

Yield: 1.693 g (9.87 mol; 98.7 % of crude product relative to the 4-nitrotoluene employed)

We claim:

1. A process for the preparation of 2-chloro-4-nitrotoluene which comprises chlorinating 4-nitrotoluene at a temperature from the melting point of said 4-nitrotoluene up to 120° C. with 0.6 to 1.2 mols of chlorine per mol of 4-nitrotoluene in a reaction mixture consisting essentially of said 4-nitrotoluene, said chlorine and 0.1 to 10 percent by weight of iodine relative to said 4-nitrotoluene.

2. A process according to claim 1 wherein the process is carried out employing 0.7 to 1.05 mols of chlorine per mol of 4-nitrotoluene.

3. A process according to claim 1 wherein the process is carried out employing 0.9 to 1.0 mol of chlorine per mol of 4-nitrotoluene.

4. A process according to claim 1 wherein the process is carried out in the presence of 0.3 to 1.0 percent by weight of iodine relative to 4-nitrotoluene.

5. A process according to claim 1 wherein the process is carried out at a temperature of 50° to 100° C.

6. A process according to claim 1 wherein the process is carried out at a temperature of from 60° to 80° C.

7. A process according to claim 1 wherein the process is carried out in the presence of a solvent.

8. A process according to claim 7 wherein said solvent is selected from the group consisting of methylene chloride, carbon tetrachloride, ethylene chloride, tetrachloroethane, a trichlorobenzene and a tetrachlorobenzene.

9. A process according to claim 1 wherein the process is carried out without addition of iron(III) chloride.